(12) United States Patent
Shvabsky et al.

(10) Patent No.: US 7,833,782 B2
(45) Date of Patent: Nov. 16, 2010

(54) APPARATUS FOR GROWING BIOLOGICAL MASS

(76) Inventors: Oleg Shvabsky, 2500 Parkview Dr., #2518, Hallandale Beach, FL (US) 33009; Jacob Gitman, 1111 Kane Concourse, #518, Bay Harbor Island, FL (US) 33154

( * ) Notice: Subject to any disclaimer, the term of this patent is extended or adjusted under 35 U.S.C. 154(b) by 92 days.

(21) Appl. No.: 12/292,190

(22) Filed: Nov. 13, 2008

(65) Prior Publication Data

US 2010/0120135 A1    May 13, 2010

(51) Int. Cl.
*C12M 1/00*      (2006.01)
*C12M 3/00*      (2006.01)

(52) U.S. Cl. ...................... 435/292.1; 47/1.4

(58) Field of Classification Search ............. 435/292.1; 47/1.4, 67 R
See application file for complete search history.

(56) References Cited

U.S. PATENT DOCUMENTS 4,253,947 A * 3/1981 Fan et al. ............... 210/610
6,602,703 B2 * 8/2003 Dutil ...................... 435/292.1

* cited by examiner

*Primary Examiner*—William H Beisner
*Assistant Examiner*—Michael Hobbs
(74) *Attorney, Agent, or Firm*—I. Zborovsky

(57) ABSTRACT

An apparatus for growing biological mass has a container for accommodating a biological mass in liquid to be grown in presence of light, a plurality of light sources in an interior of the container, a first movable plate which has passages for the light sources and which is reciprocatingly movable along the light sources to clean the latter, the first plate also having a first openings permeable for the liquid and for the biological mass, and a second plate located under the first plate and configured so that it is permeable for water and small algae fraction which have still to be grown but not permeable for the biological mass with fully grown algae, so that for discharging the biological mass the first and second plates are placed over one another and together moved toward a discharge so that the water can pass through both plates, while the biological mass is held on the first plate and moved toward the discharge to be discharged outwardly.

1 Claim, 3 Drawing Sheets

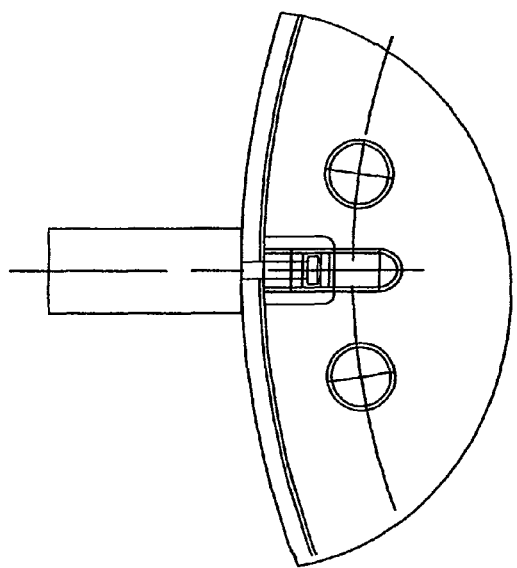
Figure 7
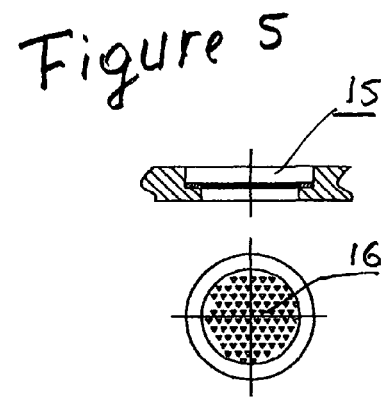
Figure 5
Figure 6
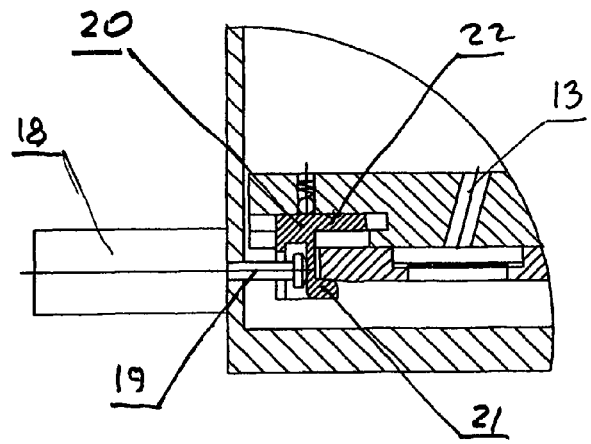
Figure 8

APPARATUS FOR GROWING BIOLOGICAL MASS

BACKGROUND OF THE INVENTION

The present invention relates to an apparatus for growing biological mass.

Apparatuses of this type are known in the art. They include a container for accommodating and growing a biological mass, light sources preferably tubular light sources arranged inside the container and generating light used, for example by a culture, and a movable plate which reciprocatingly moves in the container along the tubular light sources to clean them. One apparatus of this type is disclosed in U.S. Pat. No. 6,602,703.

In order to discharge the mass which has been grown in the apparatus, it is necessary to empty the main container accommodating the biological mass which is usually done incompletely and therefore is not efficient.

It is believed that the existing apparatuses of this type can be improved.

SUMMARY OF THE INVENTION

Accordingly, it is an object of the present invention to provide an apparatus for growing biological mass, which avoids the disadvantages of the prior art.

In keeping with these objects and with others which will become apparent hereinafter, one feature of the present invention resides, briefly stated, in an apparatus for growing biological mass, comprising a container for accommodating a biological mass in liquid to be grown in presence of light; a plurality of light sources in an interior of said container; a first movable plate which has passages for said light sources and which is reciprocatingly movable along said light sources to clean the latter, said first plate also having first openings permeable for the liquid and for the biological mass; and a second plate located under said first plate and configured so that it is permeable for water and small algae fraction which have still to be grown but not permeable for the biological mass with fully grown algae, so that for discharging the biological mass said first and second plates are placed over one another and together moved toward a discharge so that the water can pass through both plates, while the biological mass is held on the first plate and moved toward said discharge to be discharged outwardly.

When the apparatus is designed in accordance with the present invention, it is not necessary to stop a growing cycle. The discharge of the biological mass can be performed at anytime when it is desirable, for example when the volume of the biological mass increased twice. The productivity of the apparatus is increased because light is used more efficiently than in existing apparatuses where the double increase of volume takes approximately 8 hours.

A further feature of the present invention resides in that said second plate has a plurality of second openings provided with filtering elements which allow water and small algae fraction which have still to be grown to pass through said filtering elements but does not allow the biological mass with fully grown algae to pass through them.

Still a further feature of the present invention resides in providing means for providing a joint movement of said first and second plates with one another and connecting said first and second plates with one another for displacement toward the discharge, while disconnecting said plates from one another for process of growing of the biological mass and moving said first plate reciprocatingly for cleaning the light sources.

Still a further feature of the present invention resides in that the means include solenoid means providing with a lock which locks said first and second plates with one another and unlocks said first and second plates from one another.

The novel features which are considered as characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

BRIEF DESCRIPTION OF THE DRAWINGS

FIG. 3 is a plan view of a lower plate of the inventive apparatus;

FIGS. 5 and 6 are a side view and a plan view of one of the openings of the lower plate of the inventive apparatus; and FIGS. 7 and 8 are a plan view and a side view of locking means for locking plates together.

DESCRIPTION OF THE PREFERRED EMBODIMENTS

Figure 1:
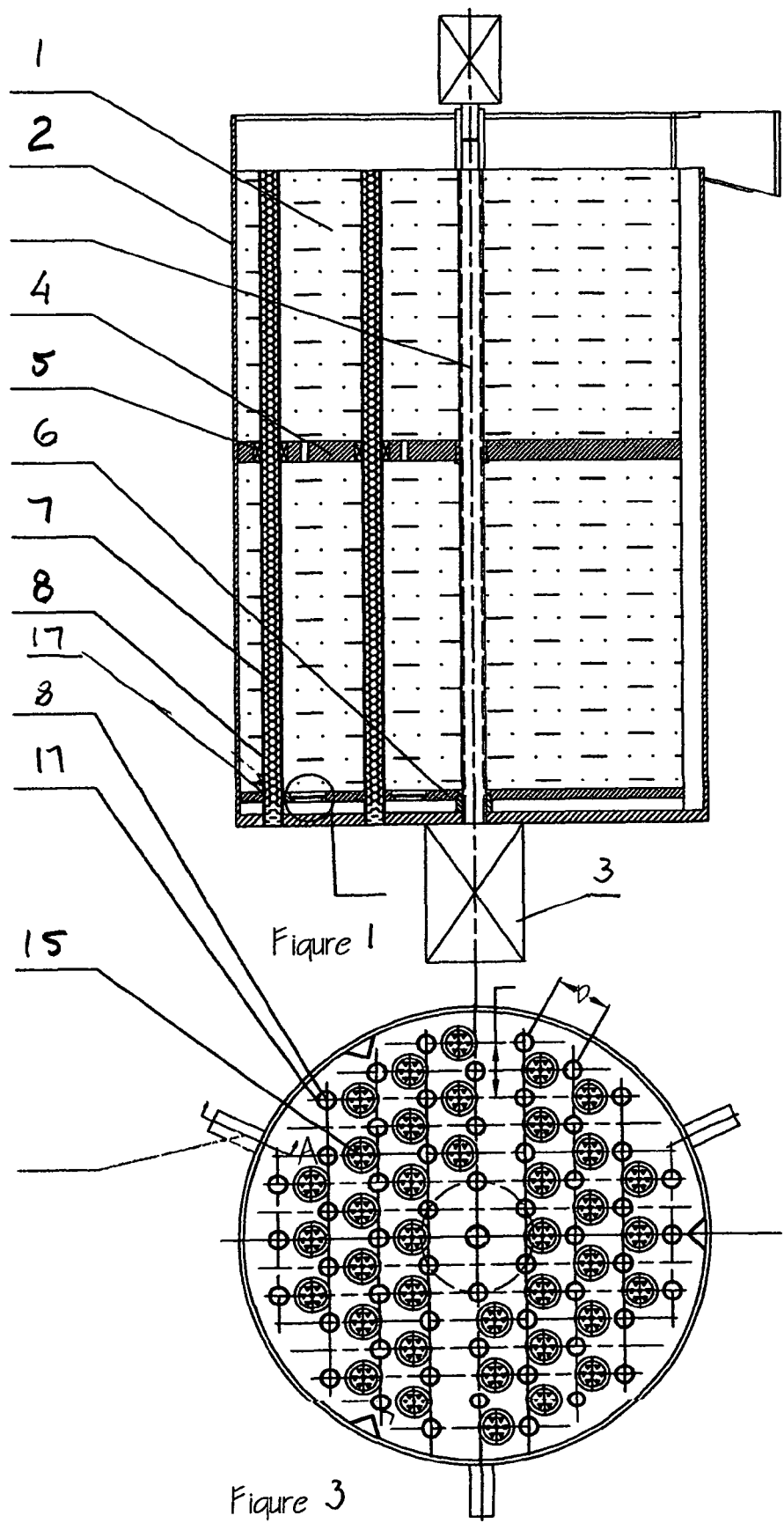
FIG. 1 is a view showing a vertical cross-section of an apparatus for growing a biological mass in accordance with the present invention with its two plates spaced from one another.
Figure 2:
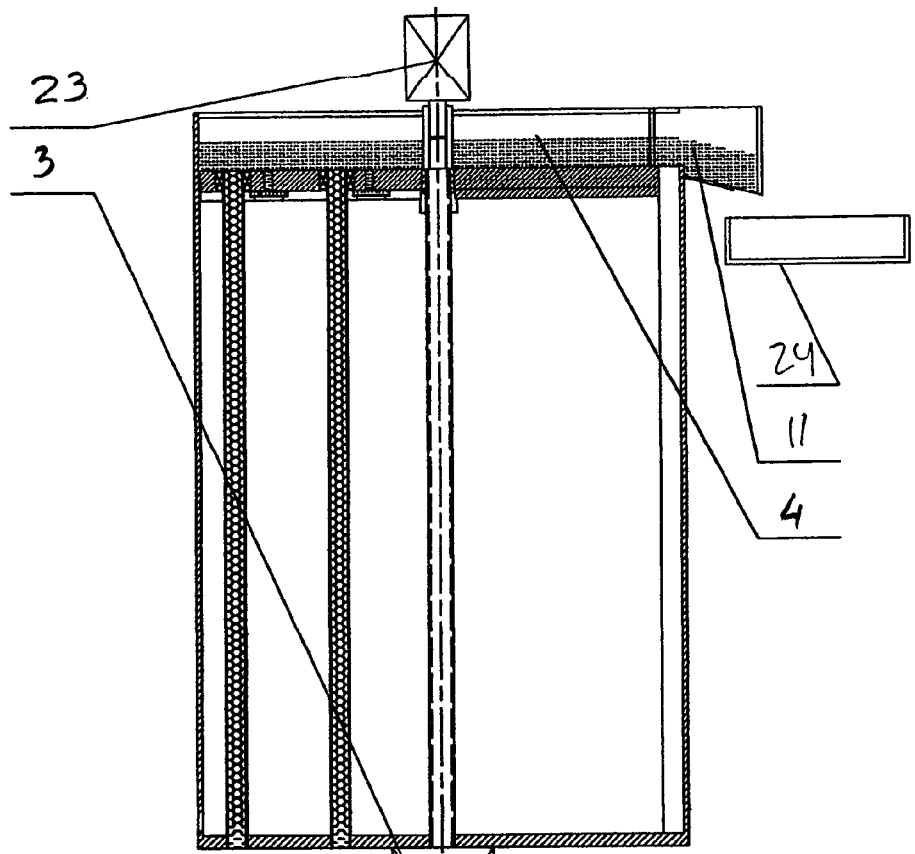
FIG. 2 is a view substantially corresponding to the view of Figure but showing the two plates which are moved together toward a discharge.
Figure 4:
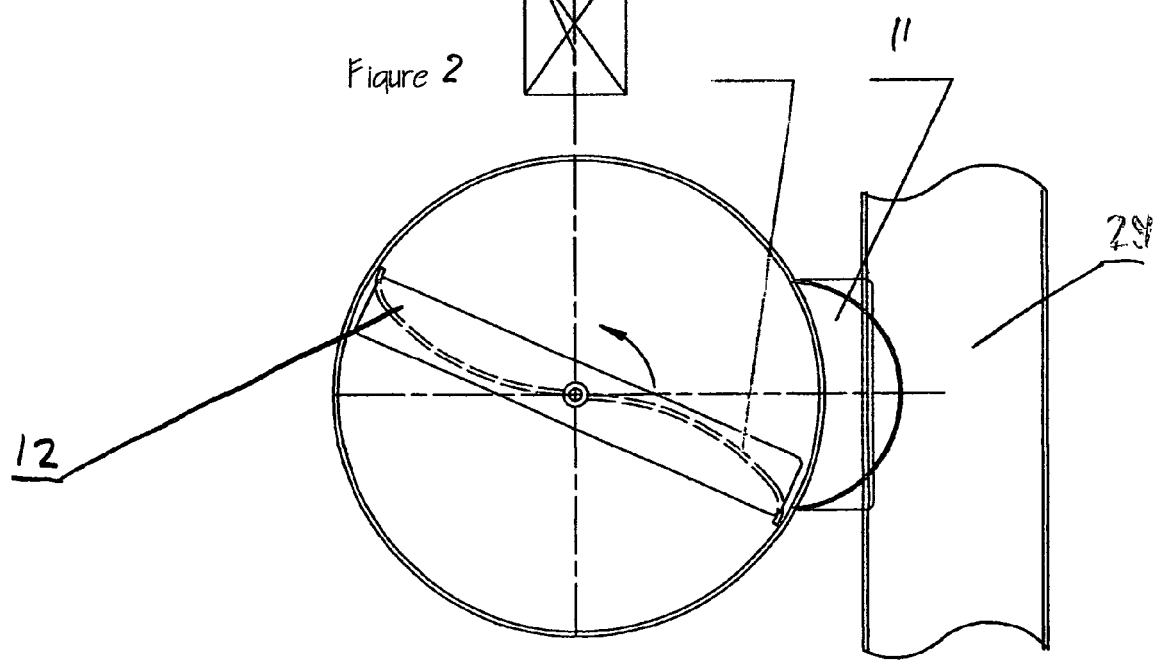
FIG. 4 is a plan view of a discharge plate of a discharge area of the inventive apparatus.

A biological mass is grown in an interior 1 of a container 2 in a liquid solution with a feedstock under the action of light 7 emitted by tubular light sources 8. the light sources are spaced from one another by equal distances. They have a spectrum which is suitable, for example light diodes. Also sunlight can be used with fiber-optic transmission to light sources.

The apparatus is provided with a first movable plate identified with reference numeral 3 which moves in the drawings up and down along the tubular light sources so as to clean surfaces 5 of the light sources. The displacement of the plate 4 is performed under the action of a screw 3 which is rotated by a motor and rotates inside a threaded opening of the plate 4. The plate 4 has a plurality of first openings for example inclined first openings identified with reference numeral 13. They are permeable both for liquid and for a biological mass.

The apparatus in accordance with the present invention further has a lower second plate 6 which is provided with a plurality of openings 15 with filtering nets 16 installed in the openings. The nets have such openings, that water and small fractions of algae to be still grown can pass through them, into fully grown algae fractions can not pass through. It also has openings 17 through which the tubular light sources 8 pass.

The inner surface of the container 2 is covered with a light-reflecting coating that intensifies the action of light on the growing biological mass.

During the process of growing of the biological mass the plate 6 is located at the bottom of the container while the plate 4 reciprocatingly moves up and down to clean the tubular light sources.

When the biological mass reaches a certain volume and it is necessary to discharge it, the second upper plate 4 is moved downwardly to lay on top of the second bottom plate 6. Locking means are used to connect them together. The locking means can include a solenoid 18 with a core 19 which displaces a locking element 20. The locking element 20 has a lower leg 21 which is designed to be configured to be placed under the lower plate 6 and a locking leg 22 which is insertable into a slot of the upper plate 4.

When the locking means is activated and its legs engage under the lower plate and into the slot of the upper plate, the plates become connected with one another. When now the motor activates the screw, the screw displaces both plates together upwardly toward a discharge. During this displacement water can pass through the openings in the upper plate and in the lower plate; however, the biological mass is retained on the top of the upper plate because it can not pass through the openings of the lower plate, since the openings of the lower plate are permeable for water but not permeable for the biological mass.

When the biological mass is displaced upwardly, it is then transported by a screw 12 provided with blades rotatable in a horizontal plane by a shaft of a further motor 23 to be moved into a collector 11 and then placed on a conveyor 29 for further processing. placed on a conveyor 24 for further processing.

It will be understood that each of the elements described above, or two or more together, may also find a useful application in other types of constructions differing from the type described above.

While the invention has been illustrated and described as embodied in an apparatus growing biological mass, it is not intended to be limited to the details shown, since various modifications and structural changes may be made without departing in any way from the spirit of the present invention.

Without further analysis, the foregoing will so fully reveal the gist of the present invention that others can, be applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An apparatus for growing biological mass, comprising a container for accommodating a biological mass in liquid to be grown in presence of light; a plurality of light sources in an interior of said container; a first movable plate which has passages for said light sources and which is reciprocatingly movable along said light sources to clean the latter, said first plate also having first openings permeable for the liquid and for the biological mass; and a second plate located under said first plate and configured so that it is permeable for water and small algae fraction which have still to be grown but not permeable for the biological mass with fully grown algae, so that for discharging the biological mass said first and second plates are placed over one another and together moved toward a discharge so that the water can pass through both plates, while the biological mass is held on the first plate and moved toward said discharge to be discharged outwardly, further comprising means for providing a joint movement of said first and second plates with one another and connecting said first and second plates with one another for displacement toward the discharge, while disconnecting said plates from one another for process of growing of the biological mass and moving said first plate reciprocatingly for cleaning the light sources, wherein said means include a lock which locks said first and second plates with one another and unlocks said first and second plates from one another, and solenoid means which act on said lock to provide locking and unlocking of said plate.

* * * * *